(12) United States Patent
Yan

(10) Patent No.: US 11,952,624 B1
(45) Date of Patent: Apr. 9, 2024

(54) NUCLEIC ACID SEQUENCING USING SELF-LUMINESCENCE

(71) Applicant: GeneSense Technology Inc., Shanghai (CN)

(72) Inventor: Mei Yan, Shanghai (CN)

(73) Assignee: GeneSense Technology Inc., Shanghai (CN), Shanghai (CN)

(*) Notice: Subject to any disclaimer, the term of this patent is extended or adjusted under 35 U.S.C. 154(b) by 0 days.

(21) Appl. No.: 18/088,097

(22) Filed: Dec. 23, 2022

Related U.S. Application Data

(63) Continuation of application No. PCT/CN2022/130269, filed on Nov. 7, 2022.

(51) Int. Cl.
*C12Q 1/68* (2018.01)
*C12Q 1/6816* (2018.01)
*C12Q 1/6869* (2018.01)
*C12Q 1/6876* (2018.01)

(52) U.S. Cl.
CPC ......... *C12Q 1/6869* (2013.01); *C12Q 1/6816* (2013.01); *C12Q 1/6876* (2013.01)

(58) Field of Classification Search
CPC ... C12Q 1/6869; C12Q 1/6816; C12Q 1/6876
See application file for complete search history.

(56) References Cited

U.S. PATENT DOCUMENTS

| | | | |
|---|---|---|---|
| 6,232,103 B1 | 5/2001 | Short | |
| 2007/0166705 A1 | 7/2007 | Milton et al. | |
| 2009/0170724 A1 | 7/2009 | Balasubramanian et al. | |
| 2010/0092957 A1 | 4/2010 | Zhao et al. | |
| 2021/0040554 A1* | 2/2021 | Ortac | C12Q 1/66 |
| 2021/0285041 A1 | 9/2021 | Ju et al. | |
| 2022/0213542 A1* | 7/2022 | Ju | C12Q 1/6869 |

FOREIGN PATENT DOCUMENTS

| | | |
|---|---|---|
| WO | 2020227953 A1 | 11/2020 |
| WO | 2021031109 A1 | 2/2021 |

OTHER PUBLICATIONS

Tan, LJ et al. Chem Comm. vol. 52, 954-957, 2016.
International Search Report on PCT/CN2022/130269, dated Apr. 23, 2023.

* cited by examiner

*Primary Examiner* — Jezia Riley
(74) *Attorney, Agent, or Firm* — Yong Chen; Lin Sun-Hoffman; Liu Chen & Hoffman LLP

(57) ABSTRACT

Methods and kits for sequencing a nucleic acid molecule are provided, which include utilizing four different compounds that are respectively derivatives of nucleotides A, (T/U), C and G, wherein the hydroxyl at the 3'-position of sugar of each of the four compounds is protected by a reversible protecting group. Each of the four compounds comprises a first linker, a second linker, and a terminal molecular label binding to or reactive to a receptor in a detectable group comprising a luminescence-activating molecule and the receptor, the luminescence-activating molecule capable of causing emission of fluorescence in the presence of a suitable substrate. The second linkers in the four compounds are different, and can be cleaved at different conditions. After incorporating one of the four compounds into a growing chain using the target nucleic acid molecule as a template, a series of reactions is performed to cleave the second linker and the first linker, and a series of detections are performed for fluorescent signals, thereby determining the identity of the nucleotide of the incorporated compound.

17 Claims, No Drawings
Specification includes a Sequence Listing.

SEQUENCE LISTING

```
Sequence total quantity: 4
SEQ ID NO: 1          moltype = DNA  length = 180
FEATURE               Location/Qualifiers
source                1..180
                      mol_type = other DNA
                      organism = synthetic construct
SEQUENCE: 1
gctcacctga caccaagtgg ctgattggtc tctgtgagag atgataccat agtgaaagct    60
cagcttctgt ctctgctgcc aactggttgg atgttcaaca gtatcggtag ttatatcagc   120
cttgttgaga gagagctcat gctgttgggc ccatgaatag cctccatctc tgctgcaatg   180

SEQ ID NO: 2          moltype = DNA  length = 10
FEATURE               Location/Qualifiers
source                1..10
                      mol_type = other DNA
                      organism = synthetic construct
SEQUENCE: 2
gctcacctga                                                           10

SEQ ID NO: 3          moltype = DNA  length = 176
FEATURE               Location/Qualifiers
source                1..176
                      mol_type = other DNA
                      organism = synthetic construct
SEQUENCE: 3
atcctgcaag caggtcagtg acagagtgtg taggtgtgta gctacctgtg gccatcggcc    60
ttcggaactc agctgtatgc ttaagaagca caccatgctg tggaggtctc cgaagctcaa   120
agaagagttc tttgggcgct gtctcagcat ctcttactac cacctgaagt cctgca       176

SEQ ID NO: 4          moltype = DNA  length = 10
FEATURE               Location/Qualifiers
source                1..10
                      mol_type = other DNA
                      organism = synthetic construct
SEQUENCE: 4
atcctgcaag                                                           10
```

NUCLEIC ACID SEQUENCING USING SELF-LUMINESCENCE

TECHNICAL FIELD

The present invention relates to nucleic acid sequencing, particularly, using single-channel sequencing methods utilizing self-luminescence patterns of different nucleotide derivatives being incorporated in a growing polynucleotide sequence.

BACKGROUND

DNA sequencing has been increasingly utilized as a powerful tool in biological and medical research. For example, in the field of cancer diagnosis and therapy, genome sequencing can provide characterizations of the genetic mutations that trigger or aid cancer development in an individual, thus providing insights into the individual's cancer risks, progression and likely response to treatment.

Various new DNA sequencing methods have been investigated to increase the efficiency and reduce cost. To date, one dominant method is sequencing by synthesis (SBS), an approach that determines DNA sequences while nucleotides are incorporated into a growing chain using the nucleic acids to be sequenced as a template.

The currently widely used high-throughput SBS technology uses cleavable fluorescent nucleotide reversible terminator (NRT) sequencing chemistry, where cleavable fluorescent NRTs are designed so that each of the four nucleotides (A, C, G, T) is modified by attaching a unique cleavable fluorophore to the base and capping the 3'OH group with a small reversible moiety so that they are still recognized by DNA polymerase as substrates. Identification of different nucleotides are accomplished based on detection of light signals of the four distinct fluorophores. More recently, SBS sequencing based on 2-channel chemistry where only two different fluorescent dyes are used for four different nucleotides. In order to read the fluorescent signals patterns, the sequencing device need to be equipped with at least two laser light sources and cameras.

WO2020227953 discloses a new sequencing method that uses a signal of a self-luminescence system to distinguish four bases of A, (T/U), C and G, without external photoexcitation. Rather, the luminescence signal used to implement the sequencing method is derived from bioluminescence. In this method, four different derivatives from A, (T/U), C and G are used, where the first derivative is linked with a first molecular label, the second derivative is linked with a second (different) molecular label, the third derivative is linked with both the first and second molecular labels, and the fourth derivative is not linked a molecular label. Two luciferases are used, each binds or be ligated to the first and second molecular label. Thus, based on the detected fluorescence signal, the identity of the base of the derivative being incorporated in a growing chain is determined.

SUMMARY

In one aspect of the disclosed subject matter, a method for sequencing a nucleic acid molecule is provided, the method comprising:

(1) providing a nucleic acid molecule to be sequenced that is linked to a support, or linking a nucleic acid molecule to be sequenced to a support;

(2) adding a primer for initiating a nucleotide polymerization reaction, a polymerase for performing the nucleotide polymerization reaction, and four compounds to form a reaction system containing a solution phase and a solid phase; wherein the four compounds are derivatives of nucleotides A, (T/U), C and G, respectively, and have the ability of base complementary pairing; wherein the hydroxyl (—OH) at the 3'-position of ribose or deoxyribose of each of the four compounds is protected by a reversible protecting group; wherein each of the four compounds takes the general formula of NT-L1-L2-Lb, where NT denotes a nucleotide of A, T(U), C, and G, L1 denotes a first linker, L2 denotes a second linker, and Lb denotes a terminal molecular label capable of binding to or reactive to a receptor in a detectable group comprising a luminescence-activating molecule and the receptor, the luminescence-activating molecule capable of causing emission of fluorescence when bound to a suitable substrate without being excited by external photoexcitation; and wherein the second linker L2 in each of the four compounds are different, denoted as L2A, L2T(U), L2C and L2G, respectively, and at least three of the second linkers are each cleavable under a condition under which the second linker in the remaining three compounds as well as the first linker of any of the four compounds are not cleaved; wherein the second linker in one of the four compounds can be optionally absent;

(3) annealing the primer to the nucleic acid molecule to be sequenced, and forming a duplex linked to the support by using the primer as an initial growing nucleic acid chain together with the nucleic acid molecule to be sequenced;

(4) using the polymerase to carry out the nucleotide polymerization reaction under a condition that allows the polymerase to carry out the nucleotide polymerization reaction, thereby incorporating one of the four compounds into the 3'-end of the growing nucleic acid chain;

(5) allowing the duplex to contact the detectable group to thereby cause a coupling reaction or specific binding between the molecular label of the incorporated compound and the receptor in the detectable group, and allowing the luminescence-activating molecule to contact the suitable substrate to undergo a fluorescence reaction, and detecting a first fluorescence signal;

(6) carrying out a first cleaving reaction at a condition suitable to cleave the second linker of a first one of L2A, L2T(U), L2C and L2G, washing off substances unattached to the support, adding the substrate to the remaining reaction system, detecting the presence or absence of a second fluorescent signal, and washing off the substrate from the reaction system;

(7) carrying out a second cleaving reaction at a condition suitable to cleave the second linker of a second one of L2A, L2T(U), L2C and L2G, washing off substances unattached to the support, adding the substrate to the reaction system, detecting the presence or absence of a third fluorescent signal, and washing off the substrate from the reaction system;

(8) carrying out a third cleaving reaction at a condition suitable to cleave the second linker of a third one of L2A, L2T(U), L2C and L2G, washing off substances unattached to the support, adding the substrate to the remaining reaction system, detecting the presence or absence of a fourth fluorescent signal, and washing off the substrate from the reaction system; and (9) based on the pattern of the presence or absence of the first, second, third, and fourth fluorescent signal, determining the identity of the nucleotide of the incorporated compound to be one of A, (T/U), C and G.

In some embodiments, step (7) is only performed when the second fluorescent signal has been detected in step (6). In some embodiments, step (8) is only performed when steps (6) and (7) have been performed and when the second fluorescent signal has been detected as present in step (6) and the third fluorescent signal has been detected as present in step (7).

In some embodiments, the method can further include: cleaving the first linker of the incorporated compound to recover the original nitrogenous base of the incorporated compound; and removing the protecting group at the 3'-position of the ribose or deoxyribose of the incorporated compound to recover the original ribose or deoxyribose of the incorporated compound.

In another aspect of the disclosed subject matter, a method of incorporating a nucleotide derivative into a nucleic acid sequence is provided, the method comprising:

combining within a reaction vessel a thermophilic nucleic acid polymerase, a primer hybridized to a portion of the nucleic acid sequence, and a nucleotide derivative, and allowing said thermophilic nucleic acid polymerase to incorporate said nucleotide derivative into said primer thereby incorporating a nucleotide derivative into a nucleic acid sequence, wherein said nucleotide derivative is one of four compounds having the general formula: NT-L1-L2-Lb, wherein NT is a nucleotide selected from A, T(U), C, and G, and the hydroxyl (—OH) at the 3'-position of ribose or deoxyribose of the nucleotide is protected by a reversible protecting group; wherein L1 is a first linker, L2 is a second linker, and Lb is a molecular label binding to or reactive to a receptor in a detectable group comprising an luminescence-activating molecule and the receptor, the luminescence-activating molecule capable of causing emission of fluorescence when bound to a suitable substrate without being excited by external photoexcitation; and wherein L2 is different for different nucleotides, and at least three of the four second linkers are each cleavable under a specific reaction condition under which L2 in other three of the four compounds as well as the first linker of any of the four compounds are not cleaved.

In another aspect of the disclosed subject matter, a kit for sequencing a nucleic acid molecule is provided, which comprises: a primer having a sequence complementary to a portion of the nucleic acid molecule and hybridizable to the portion of the nucleic acid as a template for chain extension; four compounds which are respectively derivatives of nucleotides A, (T/U), C and G, wherein the hydroxyl (—OH) at the 3'-position of ribose or deoxyribose of each of the four compounds is protected by a reversible protecting group; each of the four compounds comprises, in sequence, from the nucleotide end: a first linker, a second linker, and a terminal molecular label binding to or reactive to a receptor in a detectable group comprising an luminescence-activating molecule and the receptor, the luminescence-activating molecule capable of causing emission of fluorescence in the presence of a suitable substrate without being excited by external photoexcitation; wherein the second linker in each of the four compounds are different, designated as L2A, L2T(U), L2C and L2G, and at least three of the four second linkers are each cleavable under a specific condition under which the second linker in other three of the four compounds as well as the first linker of any of the four compounds are not cleaved; a suitable substrate, in presence of which the luminescence-activating molecule undergoes a fluorescence reaction and emits fluorescence; one or more reagents to carry out cleaving reactions to cause one of L2A, L2T(U), L2C and L2G to cleave at a condition without cleaving the other of the L2A, L2T(U), L2C and L2G; and one or more reagents to cleave the first linker and for removing the protecting group at the 3'-position of the ribose or deoxyribose of the four compounds.

In some embodiments of the disclosed methods and kits, the luminescence-activating molecule generates fluorescence by bioluminescence. In some examples, the bioluminescence-activating molecule is a luciferase and its corresponding substrate is a luciferin binding to the luciferase, which converts to oxyluciferin in oxygen which emits fluorescence.

In some embodiments of the disclosed methods and kits, the luminescence-activating molecule generates fluorescence by chemiluminescence. As an example, the chemiluminescence-activating molecule can be Horseradish Peroxidase (HRP) and its corresponding substrate can be Luminol-activating As a further example, the chemiluminescence-activating molecule can be Alkaline Phosphatase (AP), and its corresponding substrate is 3-(2'-spiroadamantyl)-4-methoxy-4-(3"-phosphoryloxy)-phenyl-1,2-dioxetane (AMPPD).

In some embodiments of the disclosed methods and kits, each of the first and second linker comprises a functional group selected from the group consisting of:

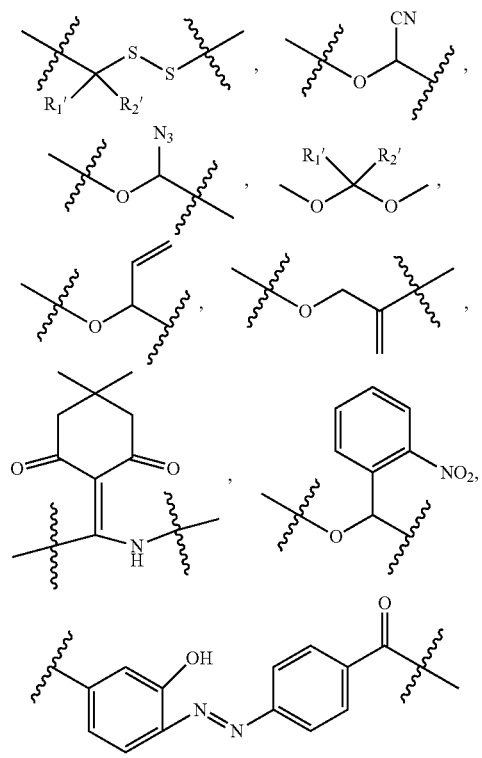

wherein R1' and R2' is independently hydrogen, halo, or $C_1$-$C_5$ alkyl.

In some embodiments of the disclosed methods and kits, the first linker of all of the four compounds is the same.

In some embodiments of the disclosed methods and kits, the molecular label of each of the four compounds is the same. In some embodiments, the molecular label for the different compounds can be different.

In some embodiments of the disclosed methods and kits, the molecular label for each of the four compounds is selected from biotin, digoxin, and N3G.

In some embodiments of the disclosed methods and kits, the molecular label for each of the four compounds comprises a functional group selected from the group consisting of:

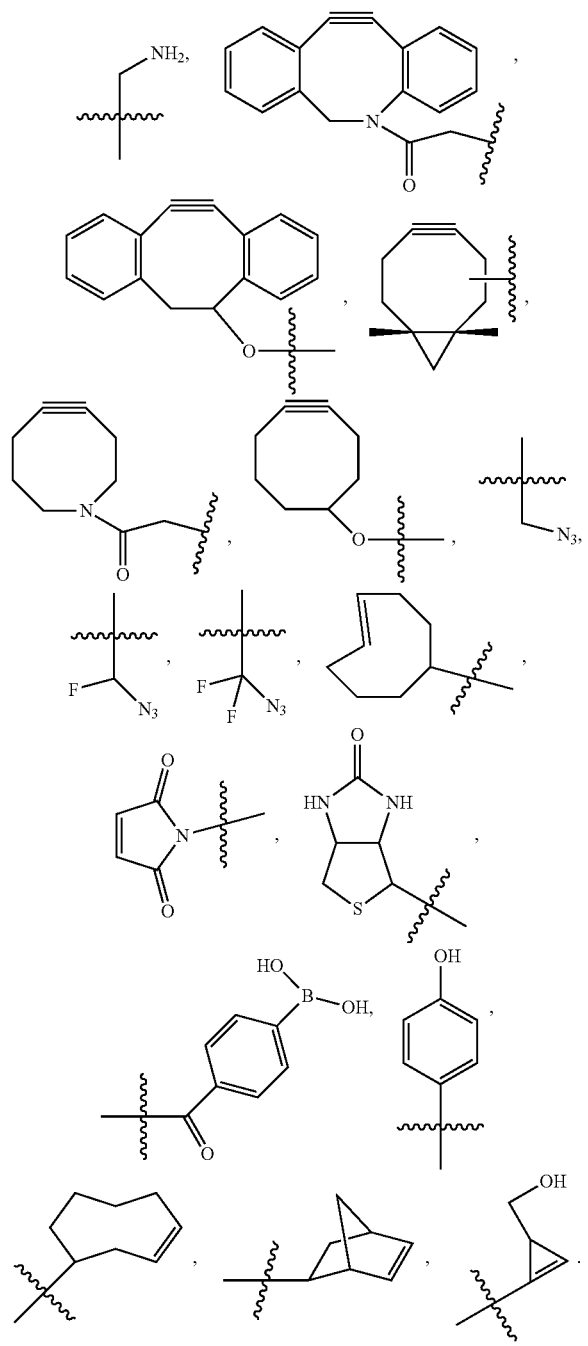

In some embodiments of the disclosed methods and kits, the receptor in the detectable group is streptavidin or a digoxin antibody.

In some embodiments of the disclosed methods and kits, the receptor in the detectable group comprises a functional group selected from the group consisting of:

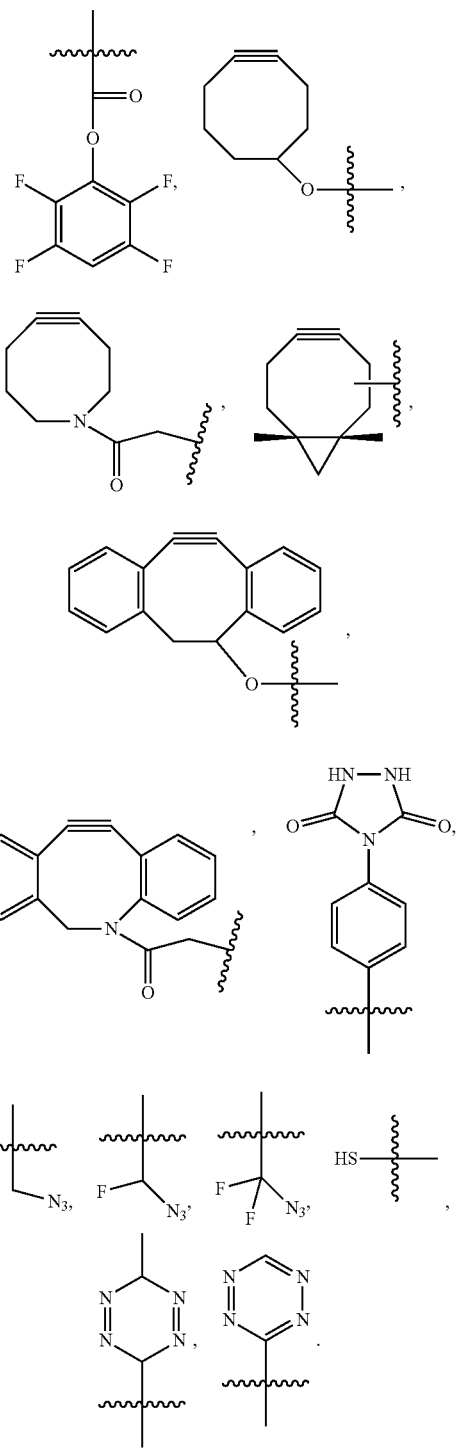

In some embodiments of the disclosed methods and kits, the reversible protecting group and the first linker both includes a functional group which can be cleaved at a same reaction condition. In some embodiments, the reversible protecting group and the first linker both includes a same functional group.

In some embodiments of the disclosed methods and kits, the reversible protecting group comprises a functional group selected from the group consisting of:

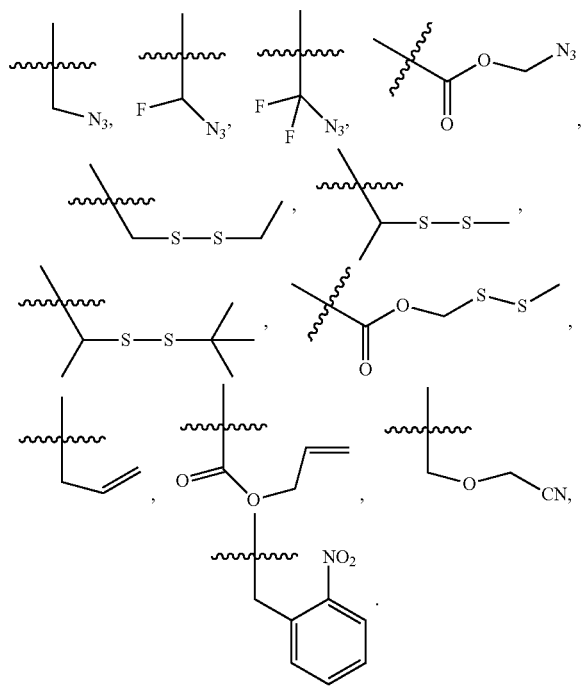

DETAILED DESCRIPTION OF EMBODIMENTS

Unless otherwise defined, all technical and scientific terms used herein have the same meanings as commonly understood by those skilled in the art to which the present invention pertains. All patents, applications and other publications mentioned herein are incorporated by reference in their entirety.

The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps but may include additional steps. When used in the context of a compound, composition, or kit, the term "comprising" means that the compound, composition, or kit includes at least the recited features or components, but may also include additional features or components.

Nucleotides as used herein usually comprises a saccharide (i.e., ribose or deoxyribose), a base, and at least one phosphate group, and includes deoxyribonucleotide, modified deoxyribonucleotide, ribonucleotide, modified ribonucleotide, peptide nucleotide, modified peptide nucleotide, modified phosphate saccharide backbone nucleoside and mixtures thereof.

As used herein, the term "polynucleotide" refers to deoxyribonucleic acid (DNA), ribonucleic acid (RNA), or analogs thereof. Polynucleotides can be single-stranded, double-stranded, or comprise both single-stranded and double-stranded sequences.

As used herein, a "reaction system" refers to a collection of reactants or chemical entities existing at a locale of a reactor or solid support (such as a SBS fluidic chamber), including primers, polymerase, target polynucleotides, nucleotide derivative compounds, luminescence-activating molecule, etc., some of which may be directly or indirectly attached to the solid support. Once a chemical is "washed off", the reaction system will not contain that chemical, and those chemical entities that are still directly or indirectly attached to the support will remain in the reaction system.

Nucleotide Derivatives

The sequencing method of the present disclosure employs nucleotide derivatives with different structures that can be cleaved at different conditions.

As used herein, the four compounds are derivatives of nucleotides A, (T/U), C and G, respectively.

The hydroxyl (—OH) at the 3'-position of ribose or deoxyribose of each of the four compounds is protected by a reversible protecting group. The protecting groups for the four compounds can be the same or different. In some embodiments, the reversible protecting group is selected from the group consisting of:

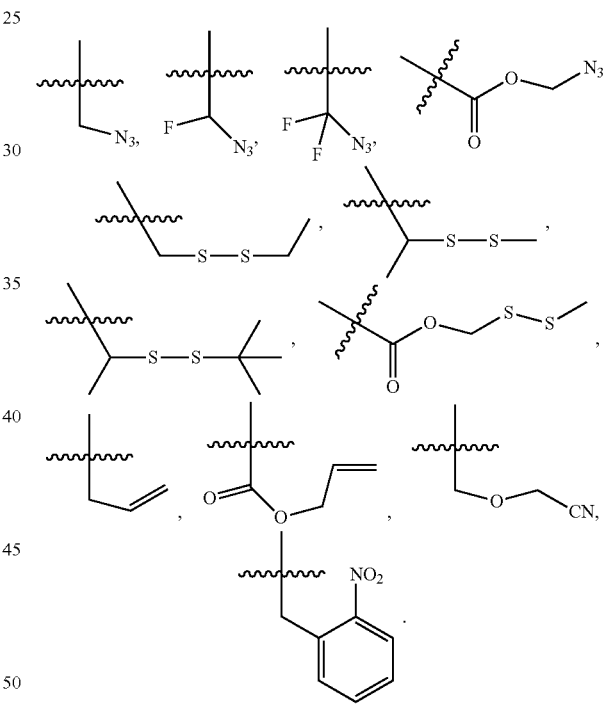

Each of the four compounds takes the general formula of NT-L1-L2-Lb, where NT denotes a nucleotide of A, T(U), C, and G, L1 denotes a first linker, L2 denotes a second linker, and Lb denotes a terminal molecular label binding to or reactive to a receptor in a detectable group comprising an enzyme molecule and the receptor, the enzyme molecule capable of causing emission of fluorescence when bound to a suitable substrate without being excited by external photoexcitation. As used herein, a molecular label being "reactive to" a receptor means that the molecular label can react to the receptor and form a covalent bond linking the molecular label and the receptor.

The second linker L2 in each of the four compounds are different, denoted as L2A, L2T(U), L2C and L2G, respectively, and at least three of the second linkers are each cleavable under a condition under which the second linker in the remaining compounds as well as the first linker are not cleaved. It is noted that the second linker in one of the four compounds can be optionally absent. In other words, in the formula NT-L1-L2-Lb, L2 can be missing for one and only one of the four compounds.

For illustration purpose, an example nucleotide (C) derivative is shown below.

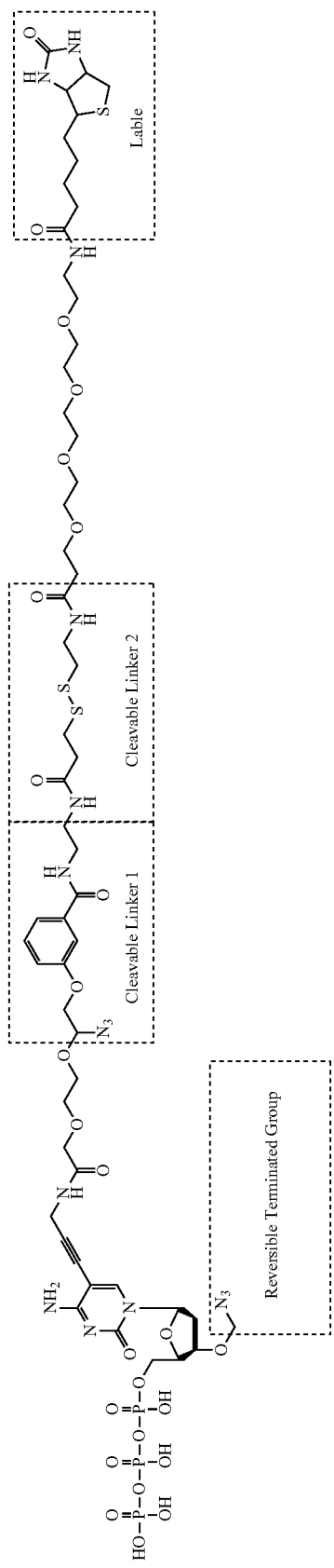

Sequencing of Polynucleotide

The nucleotide derivatives that bind to or otherwise are coupled/ligated/conjugated with the luminescence-activating molecule of the present invention are suitable for sequencing by synthesis. Sequencing by synthesis methods as used herein are various sequencing by synthesis methods well known in the art. Essentially, sequencing by synthesis includes first hybridizing a nucleic acid molecule to be sequenced with a sequencing primer, and then in the presence of a polymerase, incorporating a nucleotide derivative as described herein at the 3'-end of the sequencing primer by using the nucleic acid molecule to be sequenced as a template. After polymerization, the nucleotide is identified by detecting the fluorescent signal emitted by the luciferase. After the luciferase is removed from the labeled nucleotide, the next polymer sequencing cycle is performed.

The method for determining the sequence of a target polynucleotide can be carried out as follows: denaturing the target polynucleotide sequence, contacting the target polynucleotide with a mixture of the four nucleotide derivative compounds, so as to form a complement of the target nucleotide, and detecting the incorporated nucleotide derivative. The method utilizes polymerization, which allows the polymerase to extend the complementary strand by incorporating nucleotides complementary to the target. The polymerization reaction requires a special primer to initiate polymerization. The design of a primer suitable for chain extension is well known.

For each round of reaction, the incorporation of the nucleotide can be carried out with the aid of a suitable polymerase, such as DNA polymerase I, Klenow fragment, DNA polymerase III, T4 or T7 DNA polymerase, Taq polymerase or other engineered polymerases.

The sequencing method can be performed on the target polynucleotide arranged on a solid support. Through linker molecules, a plurality of target polynucleotides can be immobilized on the solid support, or can be attached to particles such as microspheres.

The polynucleotide can be attached to a solid support by a variety of methods, including the use of biotin-streptavidin interaction. Methods for immobilizing polynucleotides on a solid support are well known in the art. Suitable solid supports are known in the art and include glass slides and beads, ceramic and silicon surfaces, and plastic materials. The support can be flat, but microbeads or microspheres can also be used.

The necessary conditions for polymerization are well known to those skilled in the art. In order to perform the polymerase reaction, usually a primer sequence is first annealed to the target polynucleotide. The primer sequence serves as the initiating site for the subsequent extension of the complementary strand. Other conditions necessary for the polymerase reaction are well known to those skilled in the art, and these conditions include temperature, pH, and buffer composition.

Subsequently, the four compounds of the present invention are brought into contact with the target polynucleotide to enable polymerization. They can be added sequentially or at the same time. The polymerization step is allowed to proceed for a time and condition suitable to incorporate one of such compounds. Then, the unincorporated compounds are removed and leaving the duplexes attached to the support.

Then the duplex is allowed to contact the detectable group to thereby cause a coupling reaction or specific binding between the molecular label of the incorporated compound and the receptor in the detectable group. A suitable substrate for the luminescence-activating molecule is added to the reaction system, and the luminescence-activating molecule undergo a fluorescence reaction in the presence of the substrate. Depending on the choices of the luminescence-activating molecule used, different substrates can be used. For example, some luminescence-activating molecules generate fluorescence by bioluminescence, for example, a luciferase, and its corresponding substrate is luciferin binding to the luciferase. In other examples, luminescence-activating molecules generate fluorescence by chemiluminescence. As an example, the chemiluminescence-activating molecule is Horseradish Peroxidase (HRP) and its corresponding substrate can be Luminol. As a further example, the chemiluminescence-activating molecule is Alkaline Phosphatase (AP), and its corresponding substrate is 3-(2'-spiroadamantyl)-4-methoxy-4-(3"-phosphoryloxy)-phenyl-1,2-dioxetane (AMPPD).

A first fluorescence signal can then be detected at the site of the duplex. This step is not strictly necessary, because if the reaction system is set up correctly and the procedure has been performed correctly, each of the four compounds is expected to generate a fluorescent signal. However, this step can serve as a quality assurance to ensure that the reaction system is set up correctly and the procedure has been performed correctly and to minimize errors in the analysis of the patterns of signals. If no fluorescence signal is detected at this step, the procedure may be aborted and the experimental setup may be examined to determine the cause of the issue.

If the fluorescence signal is detected in this last step, a first cleaving reaction is carried out at a condition (with reactants/reagents as needed) suitable to cleave the second linker of a first one of L2A, L2T(U), L2C and L2G, and any substances unattached to the support is washed off. A buffer solution containing the substrate is added to the remaining reaction system, then the presence or absence of a second fluorescent signal is detected. If the compound incorporated comprises a second linker that happens to be cleavable in this step, then the tail end of the compound distal to the second linker in this compound will be removed together with the bound or coupled luminescence-activating molecule, and the fluorescence signal detection will be negative. Otherwise, it will remain positive.

Then, a second cleaving reaction is carried out at a condition (with reactants/reagents as needed) suitable to cleave the second linker of a second one of L2A, L2T(U), L2C and L2G. and any substances unattached to the support is washed off. A buffer solution containing the substrate is added to the remaining reaction system, then the presence or absence of a second fluorescent signal is detected. If the compound incorporated comprises a second linker that happens to be cleavable in this step, then the tail end of the compound distal to the second linker in this compound will be removed together with the bound or coupled luminescence-activating molecule, and the fluorescence signal detection will be negative. Otherwise, it will remain positive.

Then, a third cleaving reaction is carried out at a condition (with reactants/reagents as needed) suitable to cleave the third linker of a third one of L2A, L2T(U), L2C and L2G. and any substances unattached to the support is washed off. A buffer solution containing the substrate is added to the remaining reaction system, then the presence or absence of a second fluorescent signal is detected. If the compound incorporated comprises a second linker that happens to be cleavable in this step, then the tail end of the compound distal to the second linker in this compound will be removed together with the bound or coupled luminescence-activating molecule, and the fluorescence signal detection will be negative. Otherwise, it will remain positive.

Based on the pattern of the detected presence or absence of the first, second, third, and fourth fluorescent signals, the identity of the nucleotide of the incorporated compound can be determined to be one of A, (T/U), C and G.

To prepare the growing chain to incorporate further compounds, the first linker of the incorporated compound can be cleaved to recover the original nitrogenous base of the incorporated compound. The protecting group at the 3'-position of the ribose or deoxyribose of the incorporated compound can also be cleaved to recover the original ribose or deoxyribose of the incorporated compound. These two steps can be performed in any sequential order or simultaneously if possible, under suitable conditions. Subsequently, using the incorporated compound an active terminal end of the growing chain, the above outlined procedure can be repeated to incorporate another of the four compounds one at a time to the growing chain, and its identity determined.

Example 1

Specific examples of four nucleotide derivative compounds (dNTPs) used are as follows: the molecular label at the terminal end of each of the compounds is biotin, and the four compounds have four different types of cleavable second linker, which can be cleaved by known chemical reaction methods. The four compounds each have a cleavable first linker of the same type and reversible terminated group of the same type, which can be selectively cleaved by a corresponding known chemical reaction method.
Set of Compounds: dNTP Derivatives Set 1:
First Compound (dCTP Nucleotide Derivative):

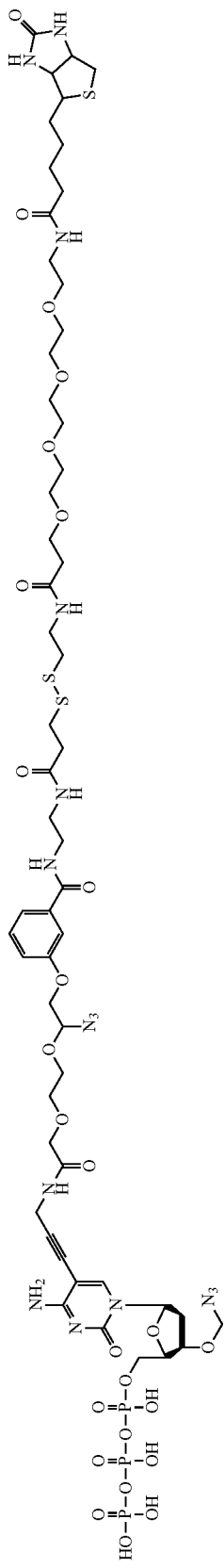
dCTP-Linker-SS-PEG4-Biotin wherein the second linker comprising

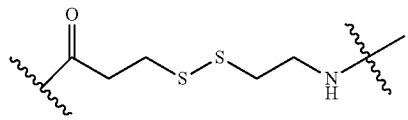 [SMILES: *NCCSSCCC(*)=O] 5 can be selectively cleaved by Dithiothreitol (DTT), and the first linker comprising

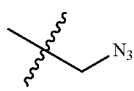 10 as well as the reversible protecting group

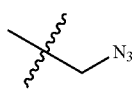 [SMILES: *CN=[N+]=[N-]] 20 can be selectively cleaved by (Tris(2-carboxyethyl)phosphine) (TCEP)

Second Compound (dTTP Nucleotide Derivative):

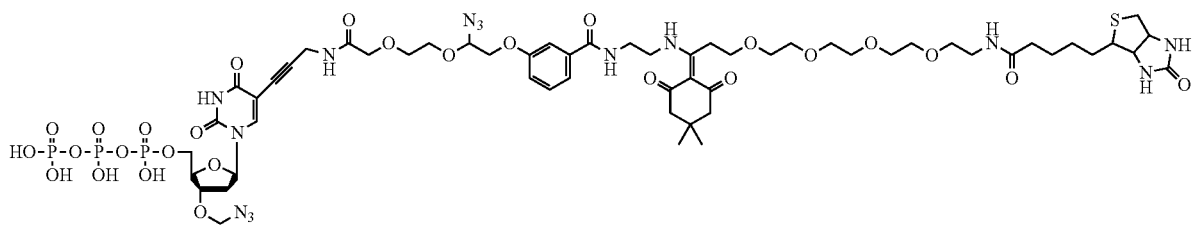

dATP-Linker-Dde-PEG4-Biotin wherein the second linker comprising

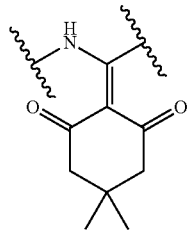 [SMILES: *NC(*)=C1C(=O)CC(C)(C)CC1=O] 40 may be selectively cleaved by hydrazine, and the first linker comprising

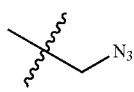 55 as well as the reversible protecting group

 60 can be selectively cleaved by (Tris(2-carboxyethyl)phosphine) (TCEP).

Third Compound (dATP Nucleotide Derivative):

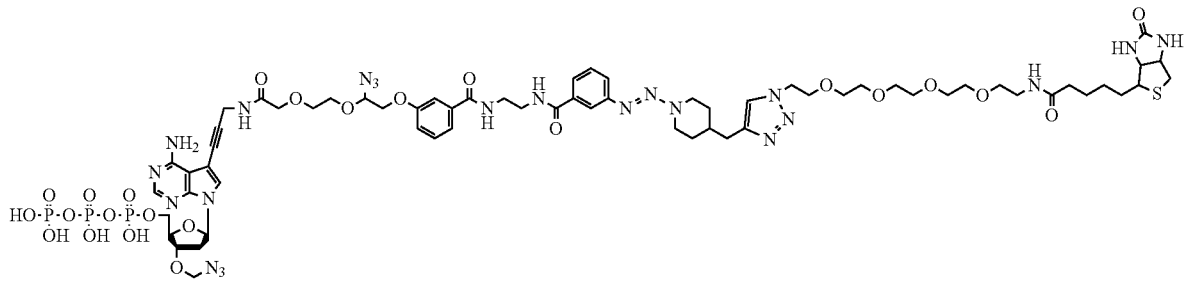

dATP-Linker-triazine-PEG4-Biotin wherein the second linker comprising

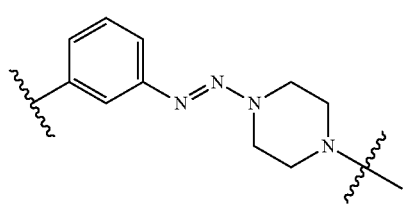 [SMILES: *c1cccc(/N=N/N2CCN(*)CC2)c1]

may be selectively cleaved by hypophosphorous acid, and the first linker comprising

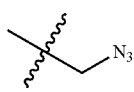 [SMILES: *CN=[N+]=[N-]]

as well as the reversible protecting group

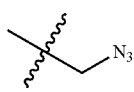 [SMILES: *CN=[N+]=[N-]]

can be selectively cleaved by (Tris(2-carboxyethyl)phosphine) (TCEP).

Fourth Compound (Nucleotide Derivative)

wherein the first linker comprising

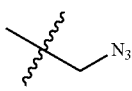

as well as the reversible protecting group

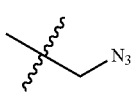

can be selectively cleaved by (Tris(2-carboxyethyl)phosphine) (TCEP). Note this example compound does not include a cleavable second linker. In other words, this compound will not cleave to release the terminal biotin (and any bound luminescence-activating molecule) under cleaving reactions performed on the other three compounds in this set.

The detectable group suitable for this set of compounds for sequencing a nucleic acid by SBS can include a streptavidin labeled HRP enzyme (SA-HRP).

Synthesis methods for the compounds in this set are shown in the below schemes:

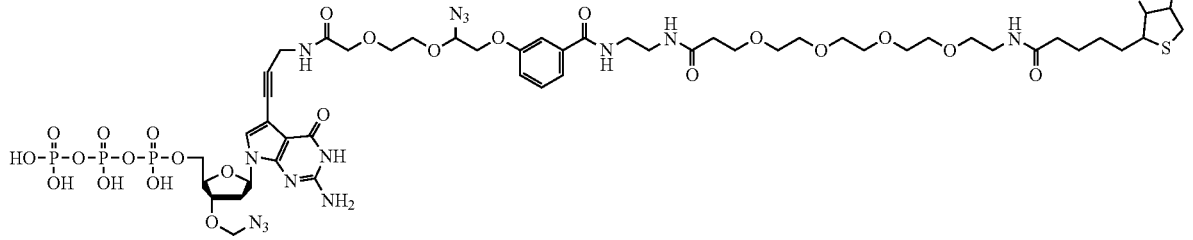

dGTP-linker-PEG4-Biotin

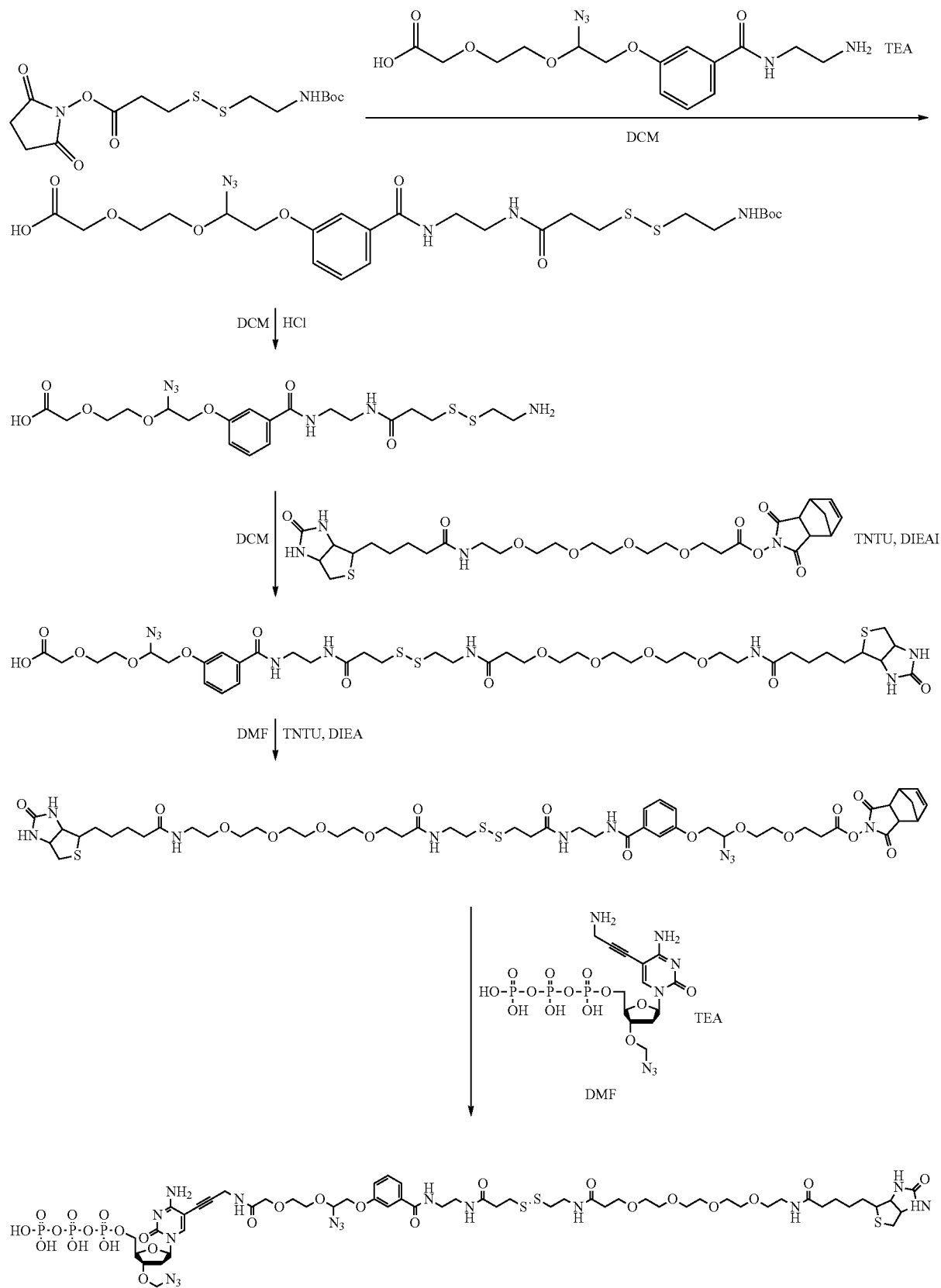

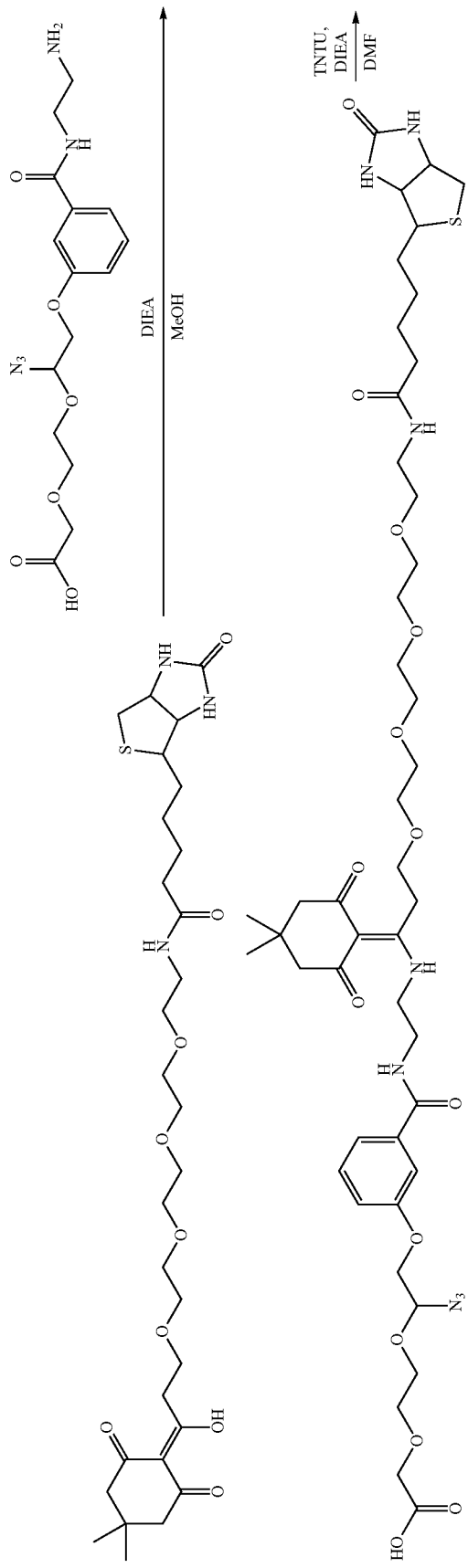

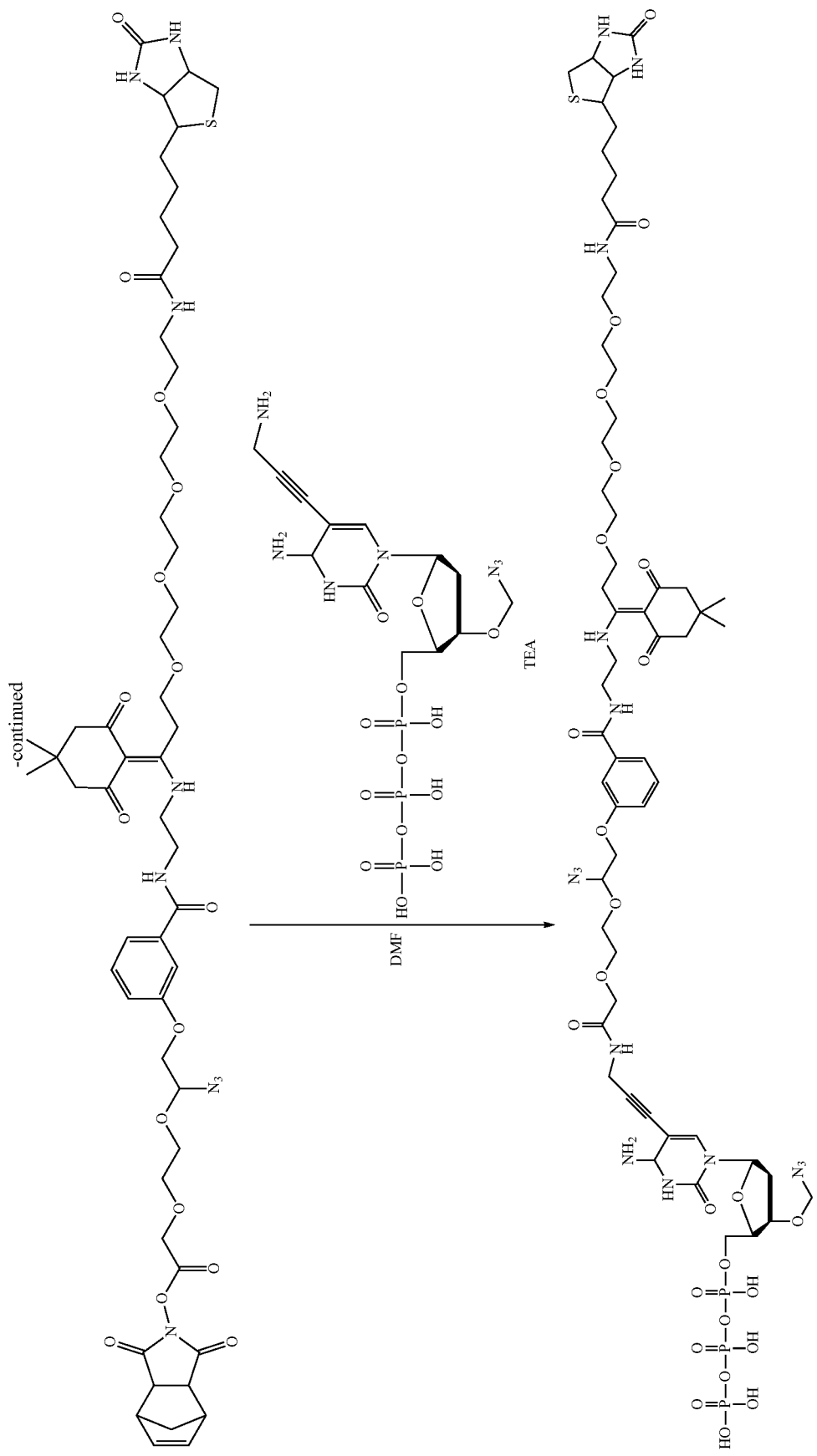

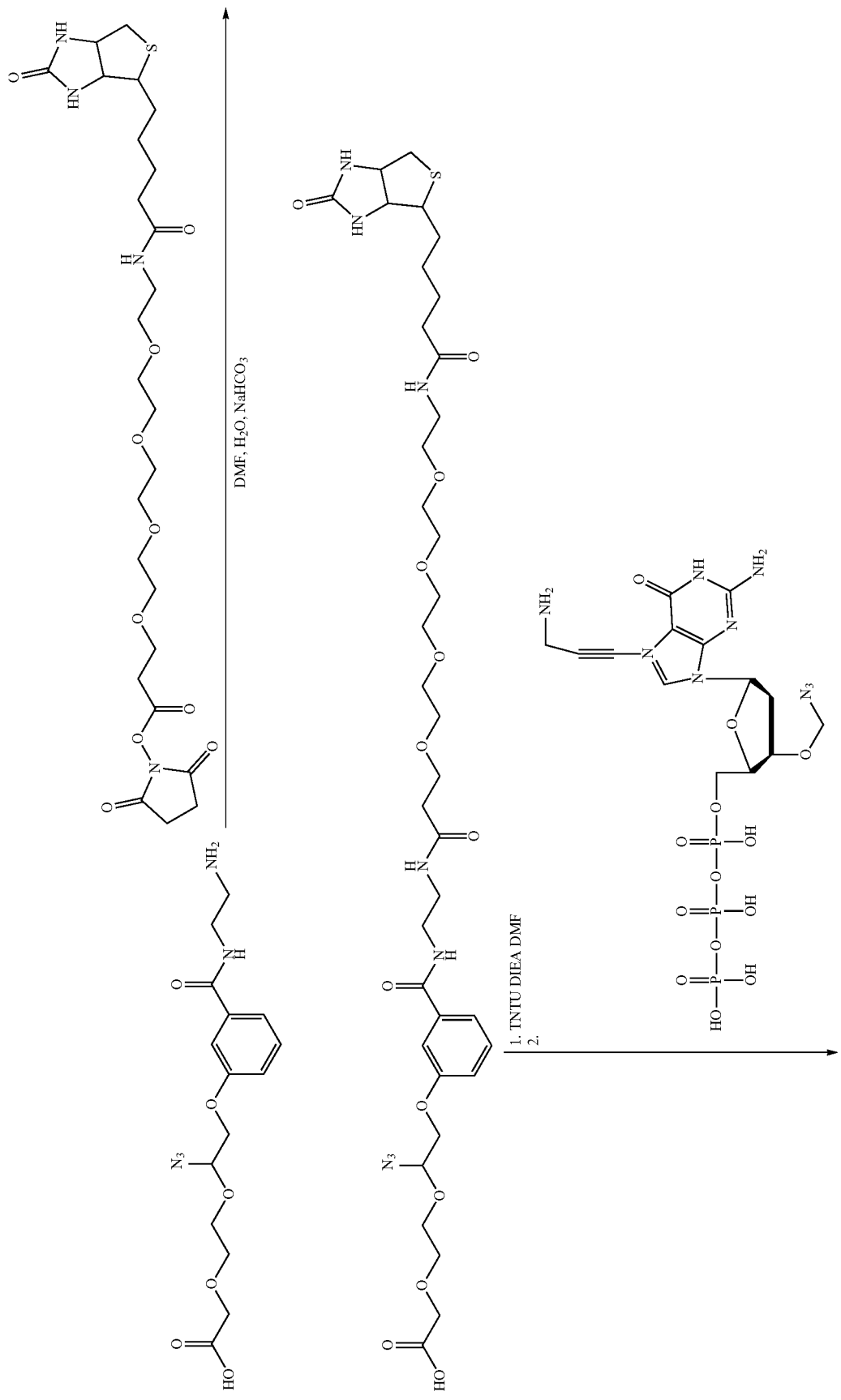

-continued
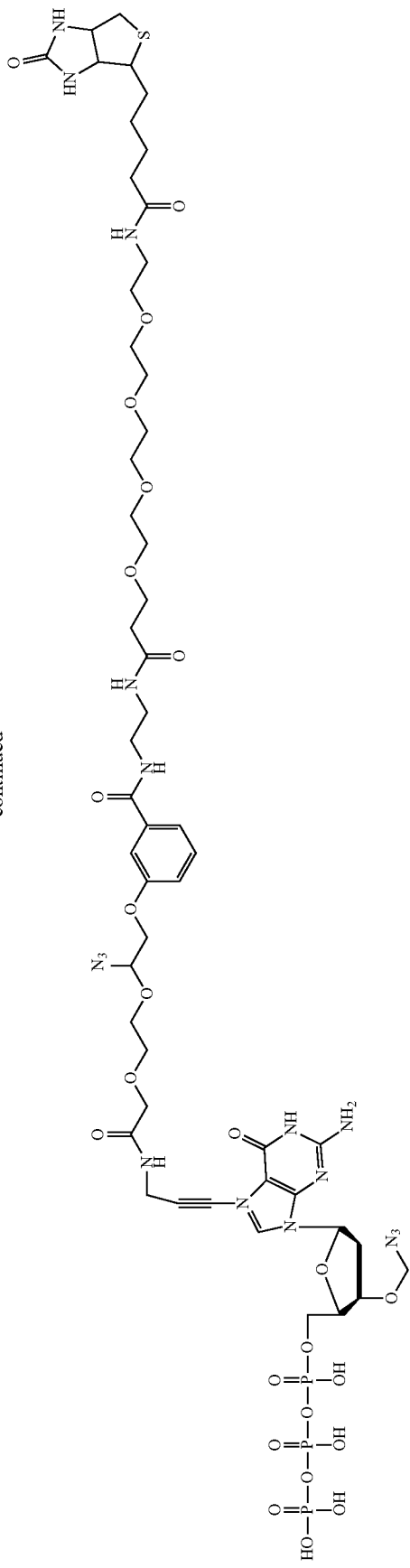

Sequencing Procedure:
(1) Preparation
A DNA fragment having the following known sequence is used as a test target:

(SEQ ID NO: 1)
GCTCACCTGACACCAAGTGGCTGATTGGTCTCTGTGAGAGATGATACCA

TAGTGAAAGCTCAGCTTCTGTCTCTGCTGCCAACTGGTTGGATGTTCAA

CAGTATCGGTAGTTATATCAGCCTTGTTGAGAGAGAGCTCATGCTGTTG

GGCCCATGAATAGCCTCCATCTCTGCTGCAATG

This target DNA sequence (together with barcode sequence and adaptor flanking on both sides of the sequence) is amplified by bridge amplification to build a cluster attached to a solid support.

(2) Sequencing:
a) Primers are first added to the DNA cluster, followed by adding a mixture of the four compounds in this set, and polymerase, and the polymerization reaction is carried out, and after the reaction is completed, a washing buffer is used to wash off reactants not directly or indirectly attached to the solid support.
b) An enzyme reaction solution containing SA-HRP is added to the reaction system and incubated at 37° C. for 2 minutes; a washing buffer is then used to wash off the enzyme reaction solution.
c) A buffer solution containing $H_2O_2$ and luminol is added to the reaction system. Detection of any fluorescence signal is performed (by taking a digital image), then a washing buffer is added to wash off the substrate buffer.
d) A first cleaving buffer solution containing DTT is added to the reaction system, and after 5 minutes of reaction at 37° C., the first cleaving buffer solution is washed off. A buffer solution containing the substrate is added, and second detection of fluorescence signal is performed (by take another digital image), and then the substrate buffer is washed off with a washing buffer;
e) A second cleaving buffer solution containing hydrazine is added, and after 5 minutes of reaction at 37° C., the second cleaving buffer is washed off. A buffer containing the substrate is added again, and a third detection of fluorescence signal is performed (by taking a further digital image), then the substrate buffer is washed off.
f) A third cleaving buffer solution containing hypophosphorous acid is added, and after 5 minutes of reaction at 37° C., the third cleaving buffer is washed off. A buffer containing the substrate is added again, and a fourth detection of fluorescence signal is performed (by taking a further digital image), then the substrate buffer is washed off.
g) A fourth cleaving buffer containing TCEP is added to cleave the first linker and remove the reversible protecting group, and after reacting at 65° C. for 3 minutes, the fourth cleaving buffer is washed off.

Steps a)-g) are repeated for the next cycle of sequencing, for a total of 10 bp sequencing.

(3) Sequencing RESULT
The pattern of detected presence/absence of fluorescence in the 10 cycles are shown in the below table. (1 indicate positive, and 0 indicates negative)

|  | Image 1 | Image 2 | Image 3 | Image 4 |
|---|---|---|---|---|
| Cycle 1 | 1 | 1 | 1 | 1 |
| Cycle 2 | 1 | 0 | 0 | 0 |
| Cycle 3 | 1 | 1 | 0 | 0 |
| Cycle 4 | 1 | 0 | 0 | 0 |
| Cycle 5 | 1 | 1 | 0 | 0 |
| Cycle 6 | 1 | 0 | 0 | 0 |
| Cycle 7 | 1 | 0 | 0 | 0 |
| Cycle 8 | 1 | 1 | 0 | 0 |
| Cycle 9 | 1 | 1 | 1 | 1 |
| Cycle 10 | 1 | 1 | 1 | 0 |

Based on the detected fluorescence signals in each cycle (4 digital images are taken for each cycle), cycle 1 and cycle 9 shows all positive detection results, therefore it can be determined that in cycles 1 and 9 it is the

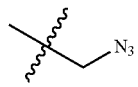

containing dGTP derivative that has been incorporated. For cycles 2, 6, and 7, after the first cleaving buffer is added, no fluorescence signals are detected in subsequent procedure, therefore it can be determined that in cycles 2, 6, 7 it is the

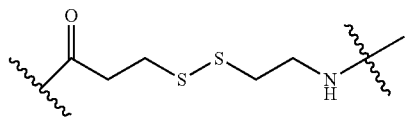 [SMILES: *NCCSSCCC(*)=O]

containing dCTP derivative that has been incorporated. For cycles 3 and 8, after the second cleaving buffer is added, no fluorescence signals are detected in subsequent procedure, therefore it can be determined that it is the

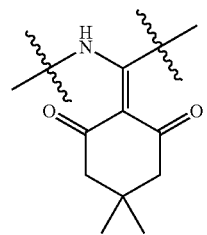 [SMILES: *NC(*)=C1C(=O)CC(C)(C)CC1=O]

containing dTTP derivative that has been incorporated in cycles 3 and 8. For cycles 5 and 10, after the third cleaving buffer is added, no fluorescence signals are detected, therefore it can be determined that

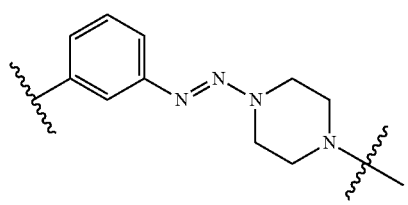 [SMILES: *c1cccc(/N=N/N2CCN(*)CC2)c1]

dATP that has been incorporated. Thus, the bases for the nucleotide sequence for the first 10 cycles can be determined to be GCTCACCTGA (SEQ ID NO:2), matching the known sequence of the DNA sequence set out to be sequenced in this example.

Example 2

Specific examples of four nucleotide derivative compounds (dNTPs) used are as follows: the molecular label at the terminal end of each of the compounds is biotin, and the four compounds have four different types of cleavable second linker, which can be cleaved by known chemical reaction methods. The four compounds each have a cleavable first linker of the same type and reversible terminated group of the same type, which can be selectively cleaved by a corresponding known chemical reaction method.

Set of Compounds: dNTP Derivatives Set 2:

First Compound (dCTP Nucleotide Derivative)

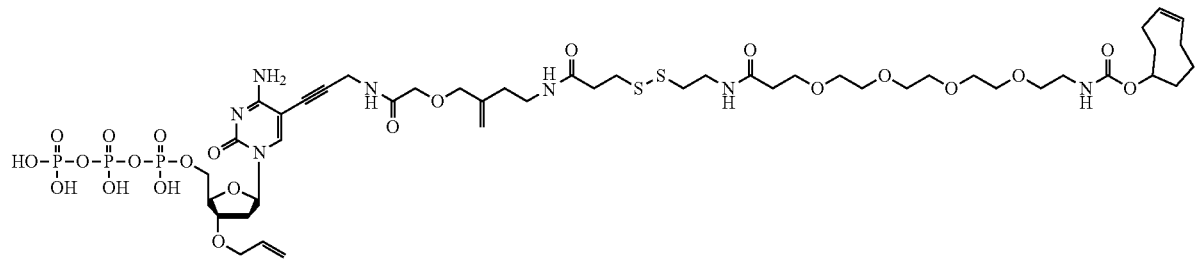

dATP-Linker-SS-PEG4-TCO where the second linker comprising

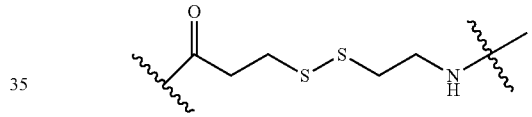

can be selectively cleaved by Dithiothreitol (DTT), and the first linker as well as the reversible protecting group comprising

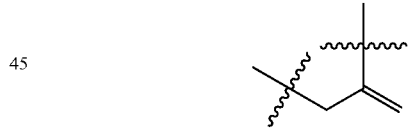

can be selectively cleaved by $Na_2PdCl_4$.

Second Compound (dTTP Nucleotide Derivative):

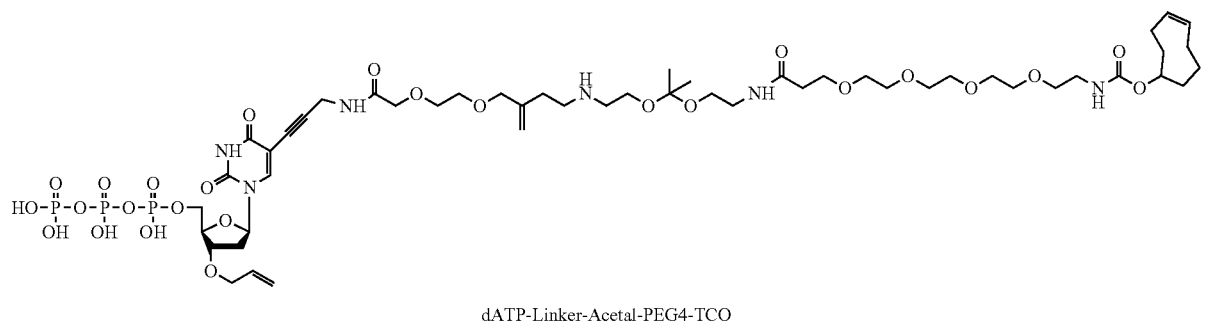

dATP-Linker-Acetal-PEG4-TCO where the second linker comprising

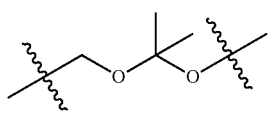 [SMILES: *COC(C)(C)O*]

can be cleaved by HCl, the first linker as well as the reversible protecting group comprising

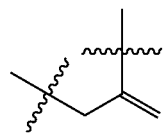 [SMILES: *CC(*)=C]

can be selectively cleaved by Na$_2$PdCl$_4$.
Third Compound (dATP Nucleotide Derivative)

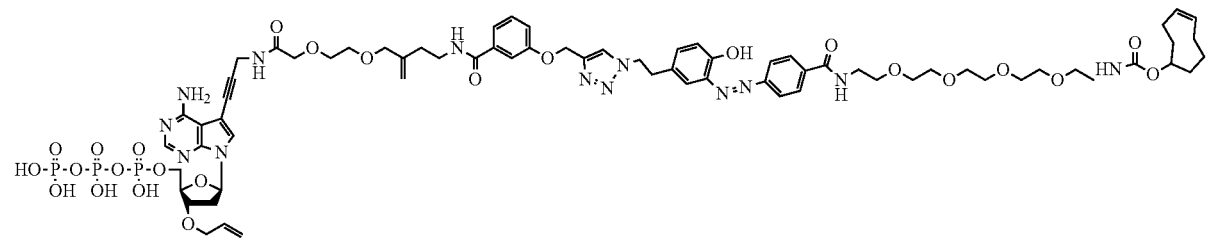

dATP-linker-diazo-PEG4-TCO where the second linker comprising

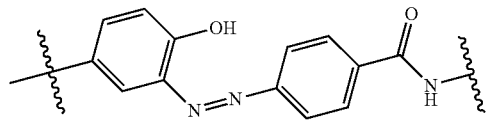 [SMILES: *NC(=O)c1ccc(N=Nc2cc(*)ccc2O)cc1]

can be selectively cleaved by sodium dithionite (Na$_2$S$_2$O$_4$), the first linker as well as the reversible protecting group comprising

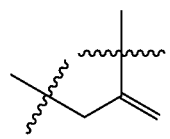 [SMILES: *CC(*)=C]

can be selectively cleaved by Na$_2$PdCl$_4$.
Fourth Compound 4 (dGTP Nucleotide Derivative)

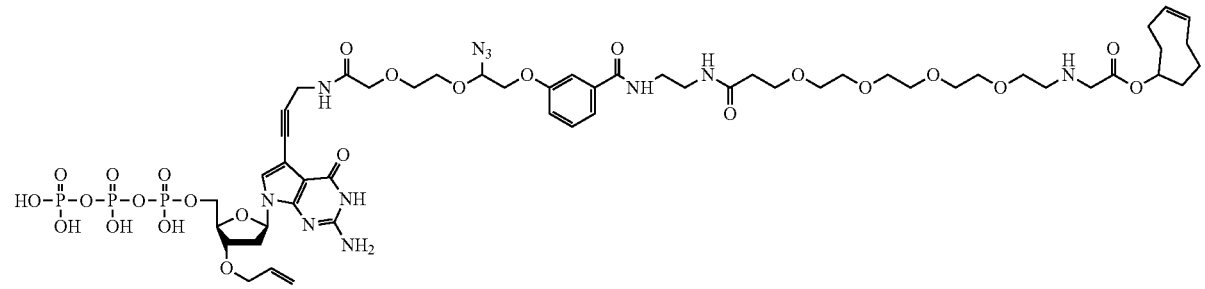

dATP-Linker-PEG4-TCO wherein the first linker comprising

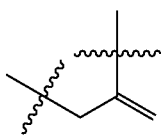

as well as the reversible protecting group

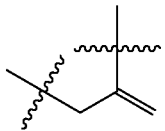 [SMILES: *CC(*)=C]

can be selectively cleaved by Na$_2$PdCl$_4$. Note this compound does not include a cleavable second linker. In other words, this compound will not cleave to release the terminal molecular label trans-cyclooctene (TCO) (and any bound luminescence-activating molecule) under cleaving reactions performed on the other three compounds in this set.

The detectable group for these set of compounds for SBS can be tetrazine-Luciferase enzyme (Tetrazine-Luc).

Synthesis methods for the compounds in this set are shown in the below schemes:

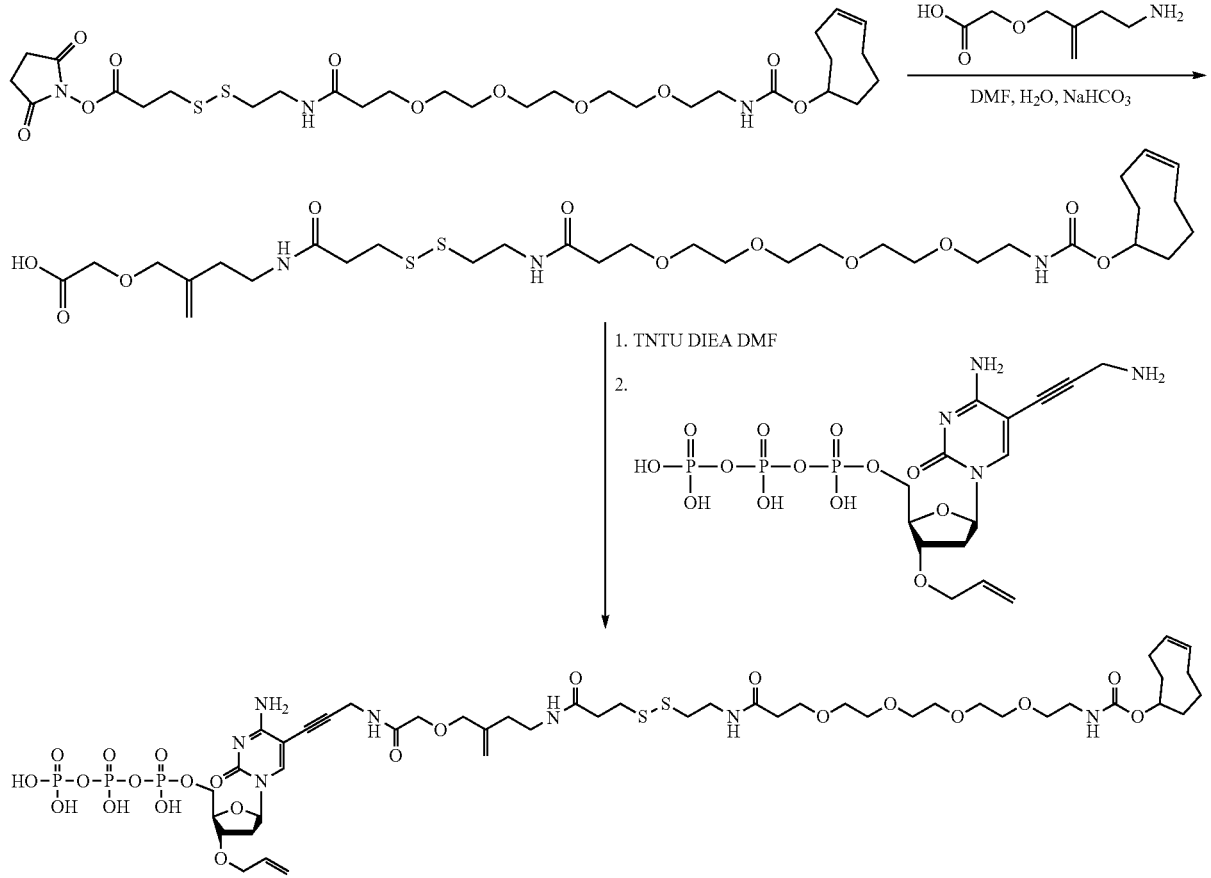

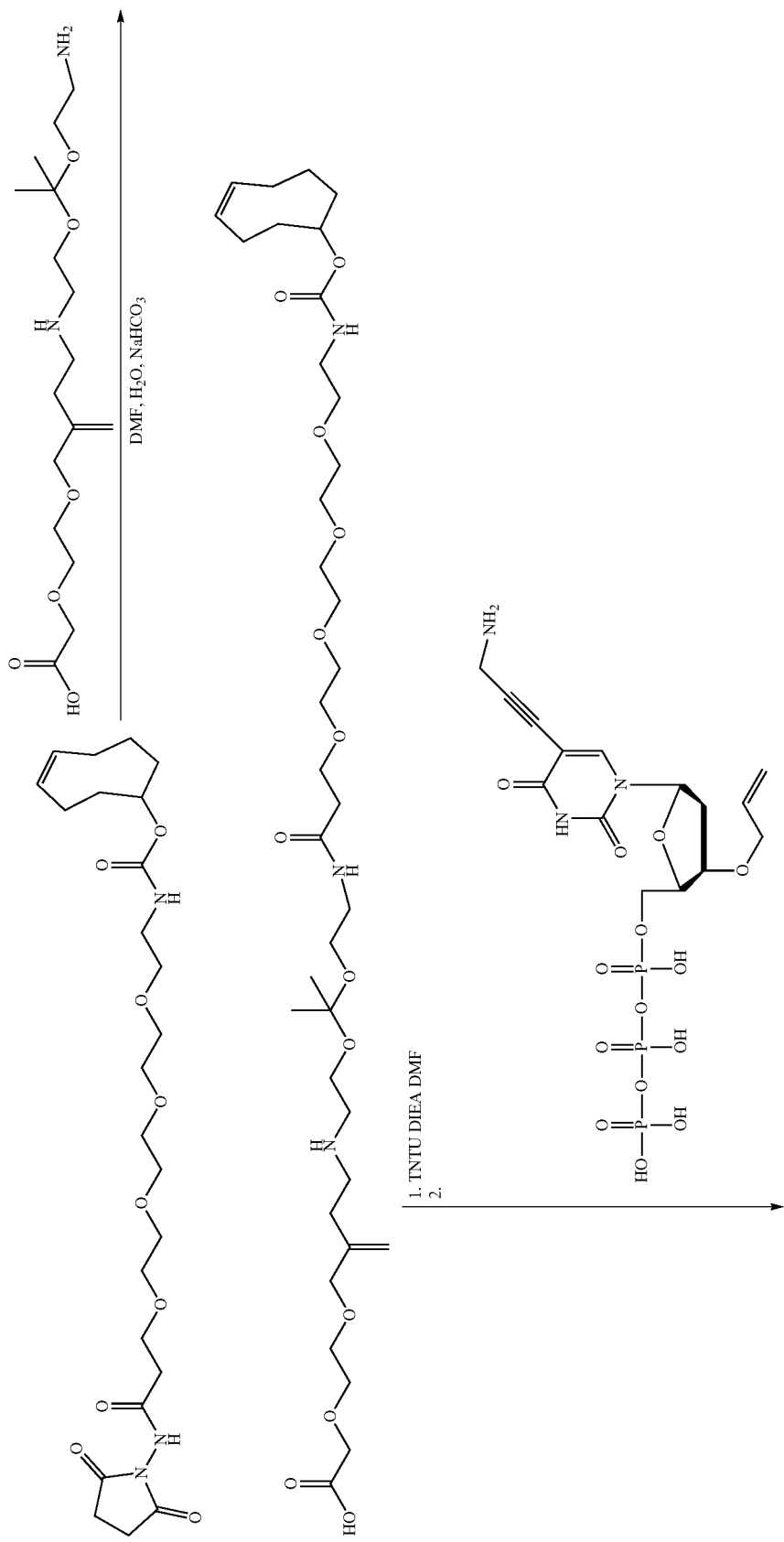

-continued
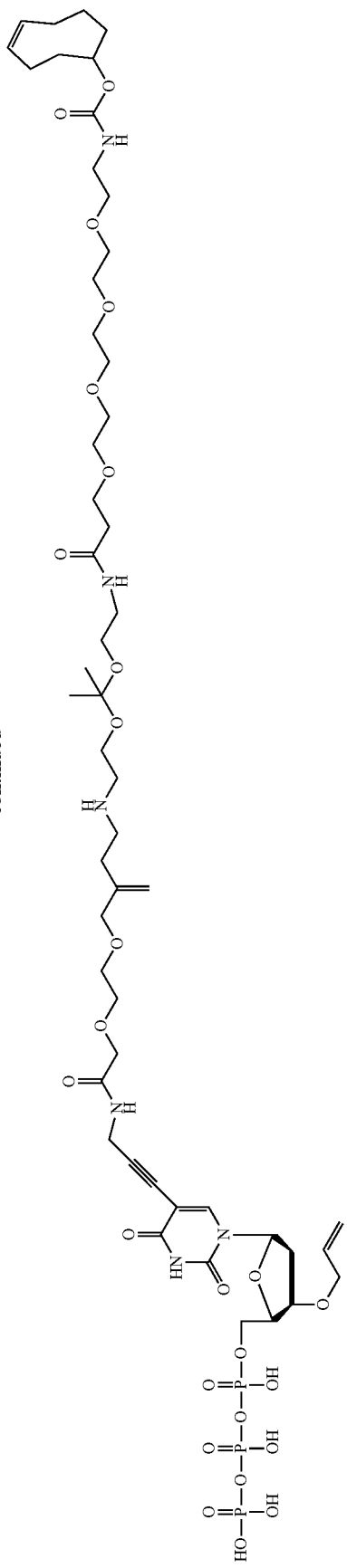

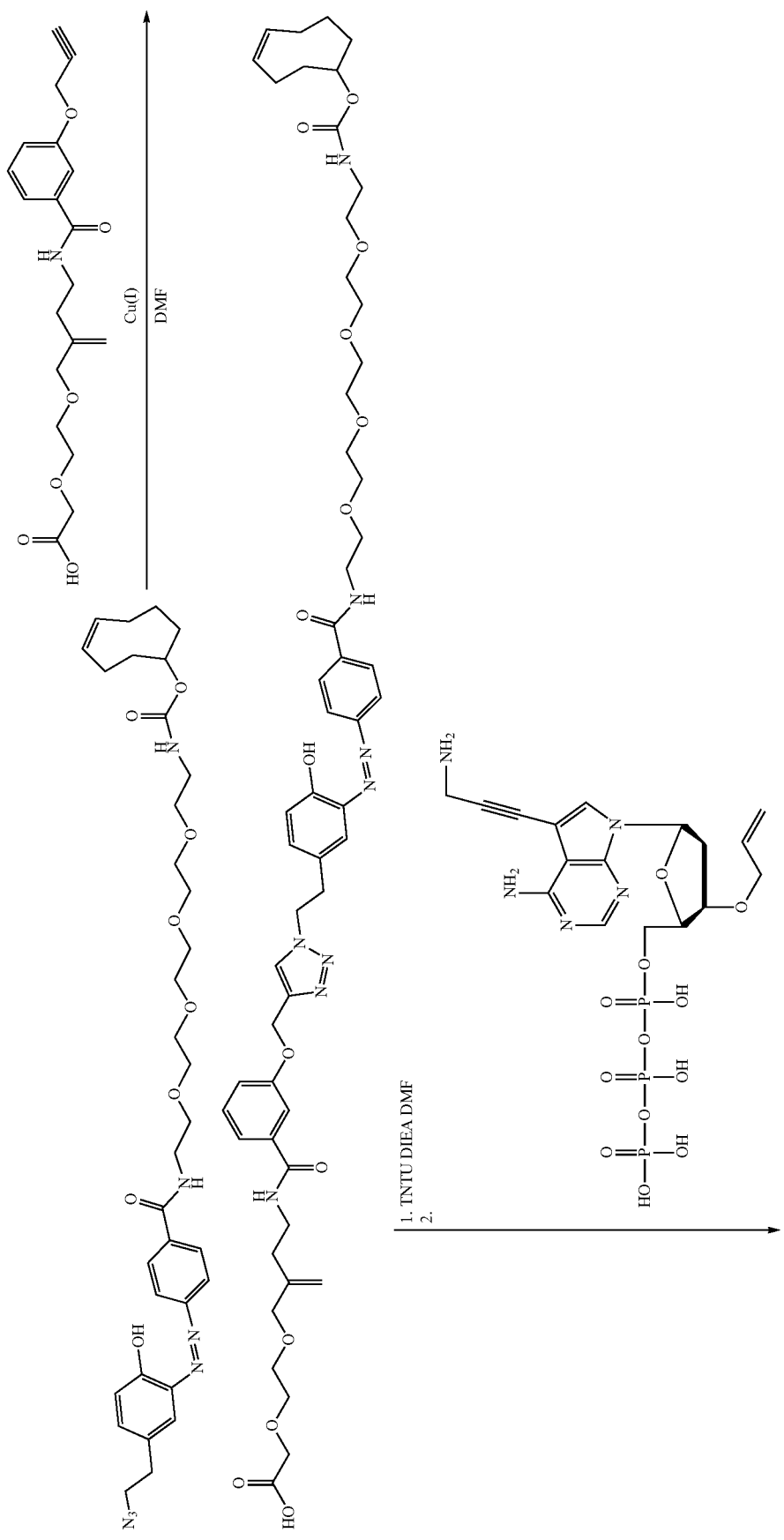

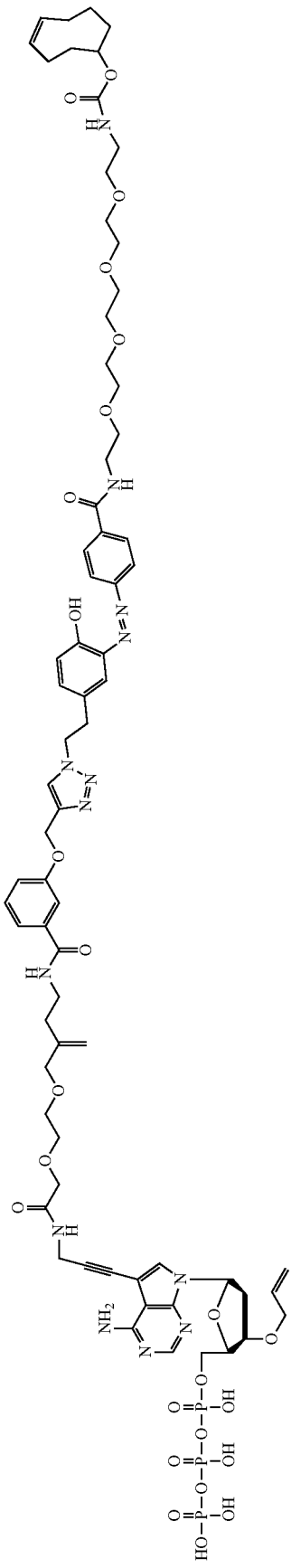
-continued

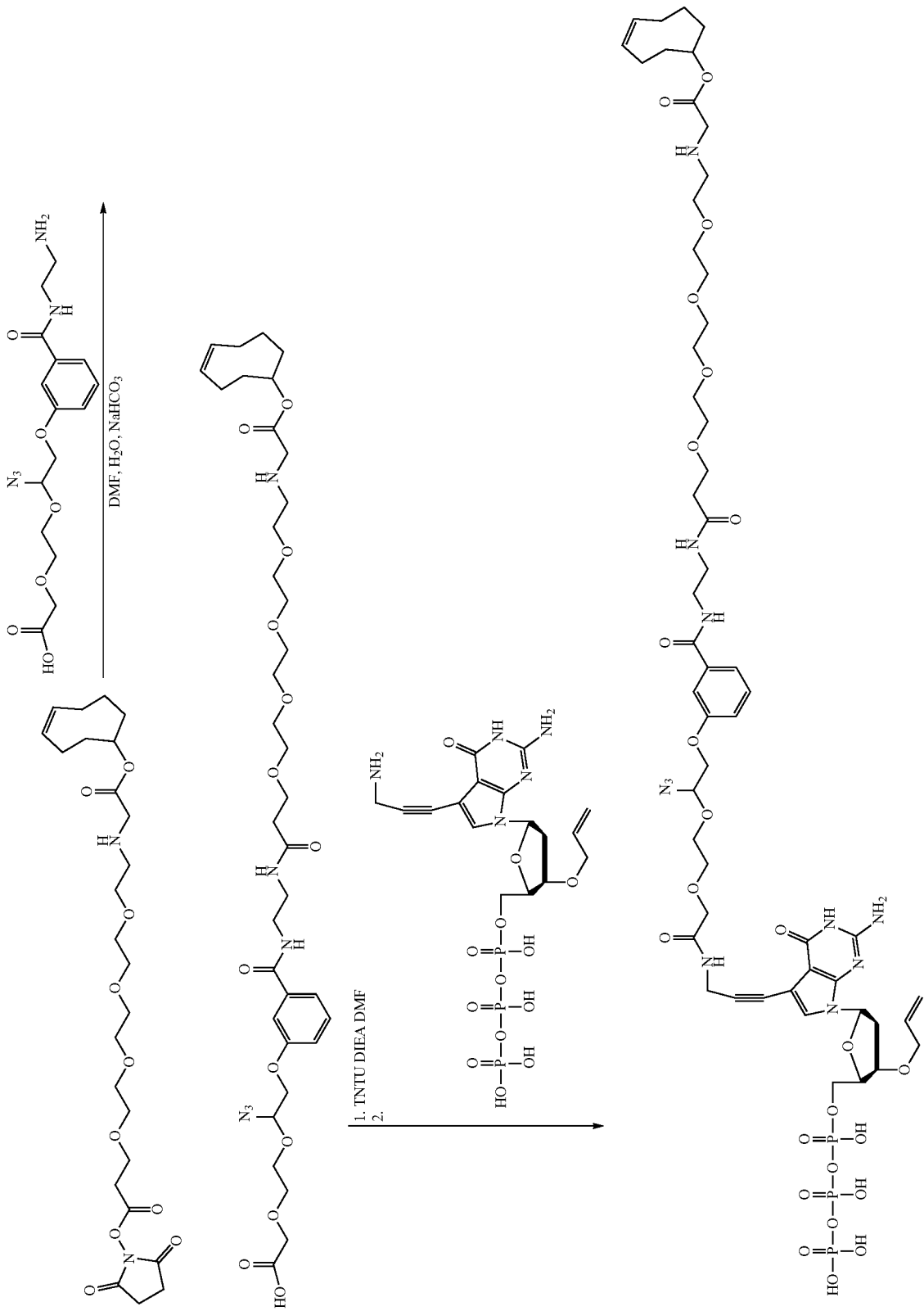

Sequencing Procedure:
(1) Preparation
A DNA fragment having the following known sequence is used as a test target:

(SEQ ID NO: 3)
ATCCTGCAAGCAGGTCAGTGACAGAGTGTGTAGGTGTGTAGCTACCTGT

GGCCATCGGCCTTCGGAACTCAGCTGTATGCTTAAGAAGCACACCATGC

TGTGGAGGTCTCCGAAGCTCAAAGAAGAGTTCTTTGGGCGCTGTCTCAG

CATCTCTTACTACCACCTGAAGTCCTGCA

This target DNA sequence (together with barcode sequence and adaptor flanking on both sides of the sequence) is amplified by bridge amplification to build a cluster attached to a solid support.
(2) Incorporation of Compounds
  a) Primers are first added to the DNA cluster, followed by adding a mixture of the four compounds in this set, and polymerase, and the polymerization reaction is carried out, and after the reaction is completed, a washing buffer is used to wash off reactants not directly or indirectly attached to the solid support.
  b) An enzyme reaction solution containing Tetrazin-luc is added to the reaction system and incubated at 37° C. for 2 minutes; a washing buffer is then used to wash off the enzyme reaction solution.
  c) A buffer solution containing luciferin is added to the reaction system. Detection of fluorescence signal is performed (by taking a digital image), then a washing buffer is added to wash off the substrate buffer.
  d) A first cleaving buffer solution containing DTT is added to the reaction system, and after 5 minutes of reaction at 37° C., the first cleaving buffer solution is washed off. A buffer solution containing the substrate is added, and second detection of fluorescence signal is performed (by take another digital image), and then the substrate buffer is washed off with a washing buffer;
  e) A fifth cleaving buffer solution containing HCl is added, and after 5 minutes of reaction at 37° C., the second cleaving buffer is washed off. A buffer containing the substrate is added again, and a third detection of fluorescence signal is performed (by taking a further digital image), then the substrate buffer is washed off.
  f) A sixth cleaving buffer solution containing $Na_2S_2O_4$ is added, and after 5 minutes of reaction at 37° C., the third cleaving buffer is washed off. A buffer containing the substrate is added again, and a fourth detection of fluorescence signal is performed (by taking a further digital image), then the substrate buffer is washed off.
  g) A seventh cleaving buffer containing $Na_2PdCl_4$ is added to cleave the first linker and remove the reversible protecting group, and after reacting at 65° C. for 3 minutes, the fourth cleaving buffer is washed off.
Steps a)-g) are repeated for the next cycle of sequencing, for a total of 10 bp sequencing.
(3) Sequencing Result
The pattern of detected presence/absence of fluorescence in the 10 cycles are shown in the below table. (1 indicate positive, and 0 indicates negative).

|  | Image 1 | Image 2 | Image 3 | Image 4 |
| --- | --- | --- | --- | --- |
| Cycle 1 | 1 | 1 | 1 | 0 |
| Cycle 2 | 1 | 1 | 0 | 0 |
| Cycle 3 | 1 | 0 | 0 | 0 |
| Cycle 4 | 1 | 0 | 0 | 0 |
| Cycle 5 | 1 | 1 | 0 | 0 |
| Cycle 6 | 1 | 1 | 1 | 1 |
| Cycle 7 | 1 | 0 | 0 | 0 |
| Cycle 8 | 1 | 1 | 1 | 0 |
| Cycle 9 | 1 | 1 | 1 | 0 |
| Cycle 10 | 1 | 1 | 1 | 1 |

Based on the detected fluorescence signals in each cycle (4 digital images are taken for each cycle), fluorescence signals in all four detections are positive in cycles 6 and 10, therefore it can be determined that in cycles 6 and 10 it is the

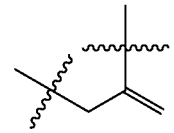

containing dGTP derivative that has been incorporated. For cycles 3, 4, and 7, after the fifth cleaving buffer is added, no fluorescence signals are detected in subsequent procedure, therefore it can be determined that in cycles 3, 4, 7 it is the

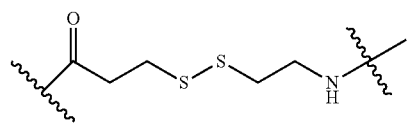 [SMILES: *NCCSSCCC(*)=O]

containing dCTP derivative that has been incorporated. For cycles 2 and 5, after the sixth cleaving buffer is added, no fluorescence signals are detected in subsequent procedure, therefore it can be determined that it is the

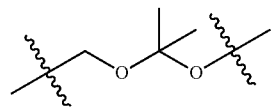 [SMILES: *COC(C)(C)O*]

containing dTTP derivative that has been incorporated in cycles 2 and 5. For cycles 1, 8 and 10, after the third cleaving buffer is added, no fluorescence signals are detected, therefore it can be determined that

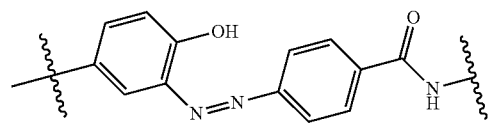

dATP that has been incorporated. Thus, the bases for the nucleotide sequence for the first 10 cycles can be determined to be ATCCTGCAAG (SEQ ID NO:4), matching the known sequence of the DNA sequence set out to be sequenced in this example.

The invention claimed is:

1. A method for sequencing a nucleic acid molecule, comprising:
(1) providing a nucleic acid molecule to be sequenced that is linked to a support, or Linking a nucleic acid molecule to be sequenced to a support;
(2) adding a primer for initiating a nucleotide polymerization reaction, a polymerase for performing the nucleotide polymerization reaction, and four compounds to form a reaction system containing a solution phase and a solid phase;
wherein, the four compounds are derivatives of nucleotides A, (T/U), C and G, respectively, each of which including a nitrogenous base, and have the ability of base complementary pairing;
wherein the hydroxyl (—OH) at the 3'-position of ribose or deoxyribose of each of the four compounds is protected by a reversible protecting group;
each of the four compounds takes the general formula of NT-L1-L2-Lb, where NT denotes a nucleotide of A, T(U), C, and G, L1 denotes a first linker, L2 denotes a second linker, and Lb denotes a terminal molecular label binding to or reactive to a receptor in a detectable group comprising a luminescence-activating molecule and the receptor, the luminescence-activating molecule capable of causing emission of fluorescence when bound to a suitable substrate without being excited by external photoexcitation;
wherein the reversible protecting group and the first linker of each of the four compounds both includes a functional group which can be cleaved at a same reaction condition;
wherein the second linker L2 in each of the four compounds are different, denoted as L2A, L2T(U), L2C and L2G, respectively, and at least three of the second linkers are each cleavable under a condition under which the second linker in the remaining compounds as well as the first linker are not cleaved; wherein the second linker in one of the four compounds can be optionally absent;
(3) annealing the primer to the nucleic acid molecule to be sequenced, and forming a duplex linked to the support by using the primer as an initial growing nucleic acid chain together with the nucleic acid molecule to be sequenced;
(4) using the polymerase to carry out the nucleotide polymerization reaction under a condition that allows the polymerase to carry out the nucleotide polymerization reaction, thereby incorporating one of the four compounds into the 3'-end of the growing nucleic acid chain;
(5) allowing the duplex to contact the detectable group to thereby cause a coupling reaction or specific binding between the molecular label of the incorporated compound and the receptor in the detectable group, and allowing the luminescence-activating molecule to contact the substrate to undergo a fluorescence reaction, and detecting a first fluorescence signal;
(6) carrying out a first cleaving reaction at a condition suitable to cleave the second linker of a first one of L2A, L2T(LT), L2C and L2G, and detecting the presence or absence of a second fluorescent signal;
(7) carrying out a second cleaving reaction at a condition suitable to cleave the second linker of a second one of L2A, L2T(U), L2C and L2G, and detecting the presence or absence of a third fluorescent signal;

(8) carrying out a third cleaving reaction at a condition suitable to cleave the second linker of a third one of L2A, L2T(U), L2C and L2G, and detecting the presence or absence of a fourth fluorescent signal;

(9) based on the pattern of the detected presence or absence of the first, second, third, and fourth fluorescent signal, determining the identity of the nucleotide of the incorporated compound to be one of A, (T/U), C and G; and

(10) cleaving the first linker of the incorporated compound while removing the protecting group at the 3'-position of the ribose or deoxyribose of the incorporated compound at a suitable reaction condition and to recover the nitrogenous base of the incorporated compound.

2. The method of claim 1, wherein each of the first and second linker comprises a functional group selected from the group consisting of:

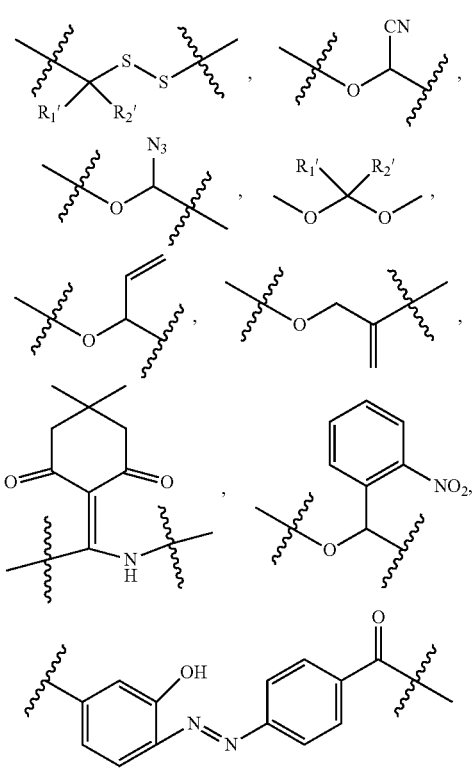

wherein R1' and R2' is independently hydrogen, halo, or $C_1$-$C_5$ alkyl.

3. The method of claim 1, wherein the first linker of each of the four compounds is the same.

4. The method of claim 1, wherein the molecular label of each of the four compounds is the same.

5. The method of claim 1, wherein the molecular label for each of the four compounds is selected from biotin, digoxin, and N3G.

6. The method of claim 1, wherein the molecular label for each of the four compounds comprises a functional group selected from the group consisting of:

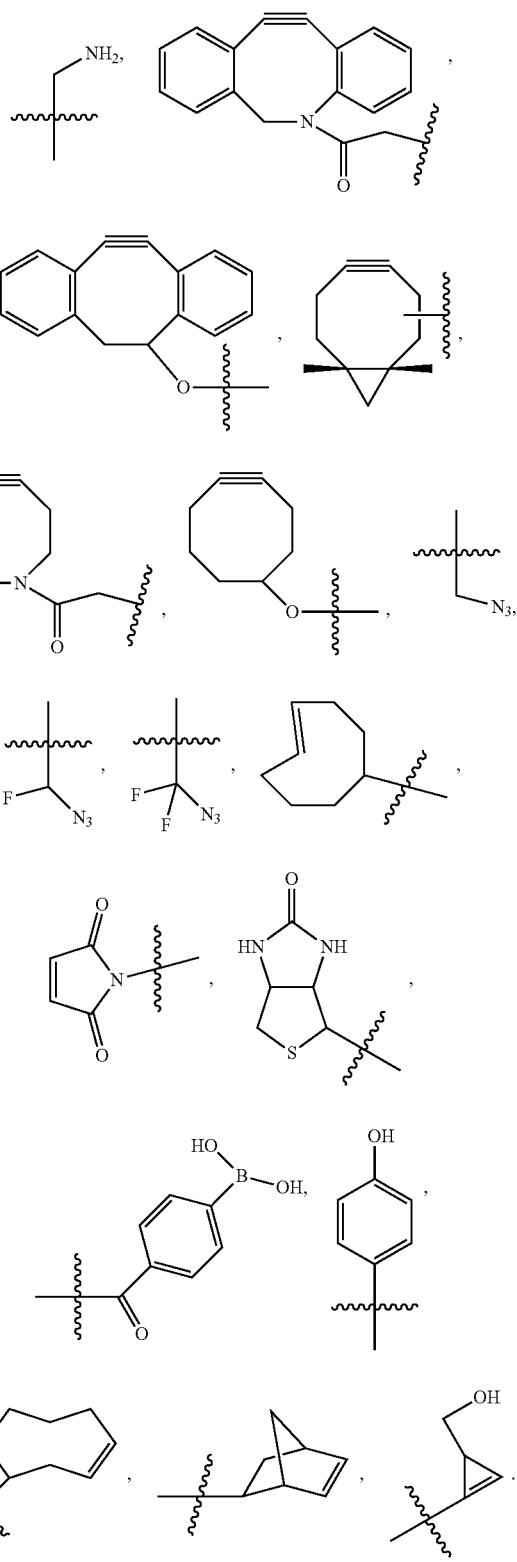

7. The method of claim 1, wherein the receptor in the detectable group is streptavidin or a digoxin antibody.

8. The method of claim 1, wherein the receptor in the detectable group comprises a functional group selected from the group consisting of:

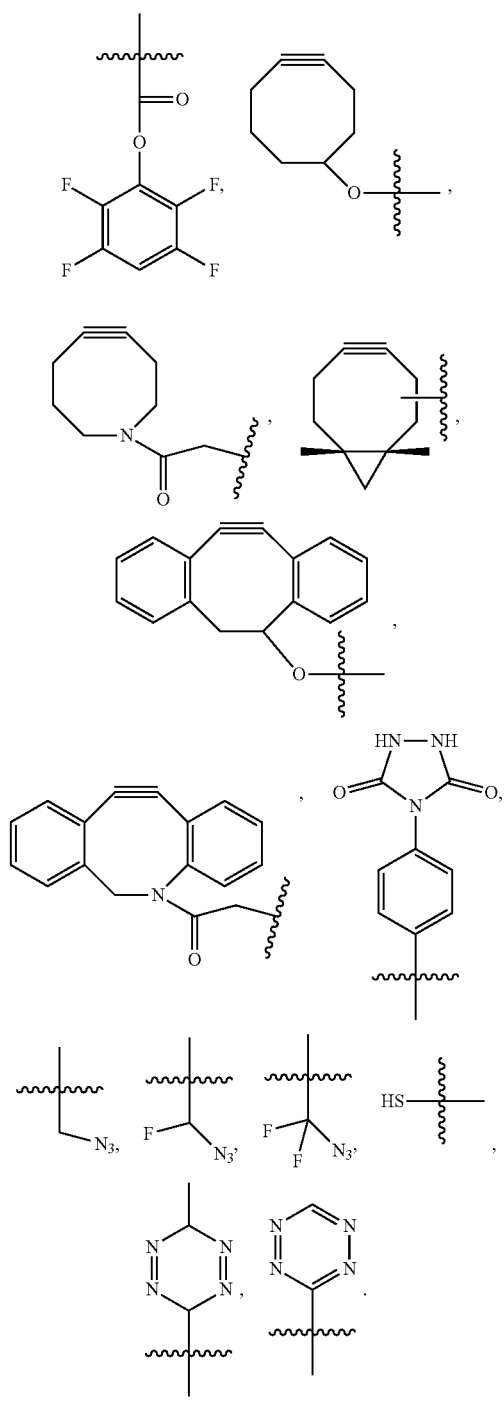

9. The method of claim 1, wherein the reversible protecting group comprises a functional group selected from the group consisting of:

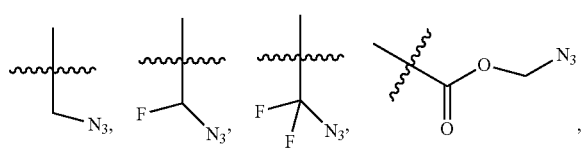

10. The method of claim 1, wherein the luminescence-activating molecule is capable of generating bioluminescence.

11. The method of claim 10, luminescence-activating molecule is luciferase and corresponding substrate luciferin.

12. The method of claim 1, wherein the luminescence-activating molecule is capable of generating chemiluminescence.

13. The method of claim 12, wherein the luminescence-activating molecule is selected from the group consisting of Horseradish Peroxidase (HRP), and Alkaline Phosphatase (AP).

14. The method of claim 1, wherein the step (7) is only performed when the second fluorescent signal has been detected in step (6).

15. The method of claim 1, wherein the step (8) is only performed when steps (6) and (7) have been performed and when the second fluorescent signal has been detected as present in step (6) and the third fluorescent signal has been detected as present in step (7).

16. A method of incorporating a nucleotide derivative into a nucleic acid sequence, comprising:
combining within a reaction vessel a thermophilic nucleic acid polymerase, a primer hybridized to a portion of the nucleic acid sequence, and a nucleotide derivative, and allowing said thermophilic nucleic acid polymerase to incorporate said nucleotide derivative into said primer thereby incorporating a nucleotide derivative into a nucleic acid sequence, wherein said nucleotide derivative is one of four compounds having the general formula:

NT-L1-L2-Lb wherein NT is a nucleotide selected from A, T(U), C, and G, and the hydroxyl (—OH) at the 3'-position of ribose or deoxyribose of the nucleotide is protected by a reversible protecting group;
wherein L1 is a first linker, L2 is a second linker, and Lb is a molecular label binding to or reactive to a receptor in a detectable group comprising an luminescence-activating molecule and the receptor, the luminescence-activating molecule capable of causing emission of fluorescence when bound to a suitable substrate without being excited by external photoexcitation; and wherein L2 is different for different nucleotides, and at least three of the four second linkers are each cleavable under a specific reaction condition under which L2 in other three of the four compounds as well as the first linker of any of the four compounds are not cleaved.

17. A kit for sequencing a nucleic acid molecule, comprising:
- a primer having a sequence complementary to a portion of the nucleic acid molecule and hybridizable to the portion of the nucleic acid as a template for chain extension;
- four compounds which are respectively derivatives of nucleotides A, (T/U), C and G, wherein the hydroxyl (—OH) at the 3'-position of ribose or deoxyribose of each of the four compounds is protected by a reversible protecting group; each of the four compounds comprises, in sequence, from the nucleotide end: a first linker, a second linker, and a terminal molecular label binding to or reactive to a receptor in a detectable group comprising an luminescence-activating molecule and the receptor, the luminescence-activating molecule capable of causing emission of fluorescence in the presence of a suitable substrate without being excited by external photoexcitation; wherein the second linker in each of the four compounds are different, designated as L2A, L2T(U), L2C and L2G, and at least three of the four second linkers are each cleavable under a specific condition under which the second linker in other three of the four compounds as well as the first linker of any of the four compounds are not cleaved;
- a suitable substrate, in presence of which the luminescence-activating molecule undergoes a fluorescence reaction and emits fluorescence;
- one or more reagents to carry out cleaving reactions to cause one of L2A, L2T(U), L2C and L2G to cleave at a condition without cleaving the other of the L2A, L2T(U), L2C and L2G; and
- one or more reagents to cleave the first linker and for removing the protecting group at the 3'-position of the ribose or deoxyribose of the four compounds.

* * * * *